United States Patent [19]

Katayama et al.

[11] Patent Number: 5,013,747

[45] Date of Patent: May 7, 1991

[54] WATER-SOLUBLE ANTISEPTIC OR ANTIFUNGAL COMPOSITION

[75] Inventors: Sakae Katayama, Osaka; Yosuke Ito, Ohtsu; Yasuhiro Nomura, Takatsuki, all of Japan

[73] Assignee: Katayama Chemical, Inc., Japan

[21] Appl. No.: 432,568

[22] Filed: Nov. 7, 1989

Related U.S. Application Data

[63] Continuation-in-part of Ser. No. 230,165, Aug. 9, 1988, abandoned.

[30] Foreign Application Priority Data

Aug. 26, 1987 [JP] Japan .................................. 62-212422

[51] Int. Cl.⁵ .................................................. A61K 31/425
[52] U.S. Cl. ........................................ 514/367; 514/975
[58] Field of Search ................................. 514/367, 975

[56] References Cited

U.S. PATENT DOCUMENTS 3,520,976  7/1970  Buchman et al. ................... 514/367

*Primary Examiner*—Stanley J. Friedman
*Assistant Examiner*—Zohreh A. Fay
*Attorney, Agent, or Firm*—Bryan, Cave, McPheeters & McRoberts

[57] ABSTRACT

A water-soluble antiseptic or antifungal composition containing 2-(thiocyanomethylthio)benzothiazole as the active ingredient, a polyoxyalkylene styrylphenyl ether phosphoric acid ester, or alkali metal salt thereof as a surfactant and an organic solvent. The composition forms a clear solution which is stable for long periods of time and which can be diluted with water.

14 Claims, No Drawings

WATER-SOLUBLE ANTISEPTIC OR ANTIFUNGAL COMPOSITION

This is a continuation-in-part of application Ser. No. 07/230,165 filed Aug. 9, 1988, now abandoned.

BACKGROUND OF THE INVENTION

This invention relates to a water-soluble antiseptic or antifungal composition containing 2-(thiocyanomethylthio) benzothiazole as the active ingredient.

2-(Thiocyanomethylthio)benzothiazole (hereinafter abbreviated as TCMTB) is a known compound for non-medical uses as an antiseptic or antifungal agent, which is used to treat wood, natural leathers, plants, seeds, and the like. Since TCMTB is insoluble in water, in preparing it as a solution for practical use, it must be dissolved in an organic solvent, alone or together with certain surfactants. In actual usage, the solution of TCMTB in an organic solvent is further diluted with an organic solvent to the desired concentration and applied, for instance, to wood. Alternatively, the solution of TCMTB in an organic solvent to which a surfactant is added can be diluted with water, thereby forming an emulsion of the oil in water type. Such emulsions can be used for a variety of purposes but they have drawbacks since the emulsions lack stability; and, permeability of the emulsion into the inner portion of materials such as wood and natural leather remains limited.

Various preparations of water-insoluble antiseptic and antifungal substances other than TCMTB have been proposed e.g., see Japanese Patent Publication Nos. Sho 44(1969)-31221 and Sho 51(1976)-50483; Japanese Unexamined Patent Publication Nos. Sho 51(1976)-9705, Sho 52(1977)-66603 and Sho 57(1982)-22003.

This invention is directed to solving the drawbacks of the TCMTB emulsions as mentioned above and to find TCMTB compositions which can form a stable aqueous solution (not an emulsion) by diluting with water. Such compositions would show an improved permeability to the inner portions of materials to be treated.

We have investigated the combinations of TCMTB with various surfactants and organic solvents and have found that the use of polyoxyalkylene styrylphenyl ether phosphoric acid esters or the alkali metal salts thereof, can solve the above mentioned problems.

SUMMARY OF THE INVENTION

This invention provides a water-soluble antiseptic or antifungal composition which comprises 2-(thiocyanomethylthio)benzothiazole in an amount of 1–40% by weight of the composition, a polyoxyalkylene styrylphenyl ether phosphoric acid ester or alkali metal salt thereof in an amount of 5–40% by weight of the composition and an organic solvent which can dissolve the above benzothiazole compound and is compatible with water.

PREFERRED EMBODIMENTS OF THE INVENTION

TCMTB of the antiseptic and antifungal active ingredient of the invention, has the following structure:

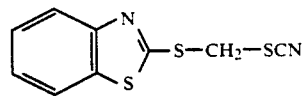

and may be employed in pure form, which however is not required for non-medical uses. For example, the purity would be sufficient if it is about 80% or more. TCMTB having such purity is commercially available as Busan 80 (Trademark of Buckman Labo., U.S.A.) and hence is easily utilized.

The surfactants to be used in the invention are polyoxyalkylene styrylphenyl ether Phosphoric acid esters (hereinafter abbreviated as STP) prepared in accordance with Japanese unexamined Patent Publication No. 56 (1981) - 120558 (Examples 1-3), or the alkali metal salts thereof. These surfactants are believed to show both nonionic and anionic properties and can be represented by the formula (2):

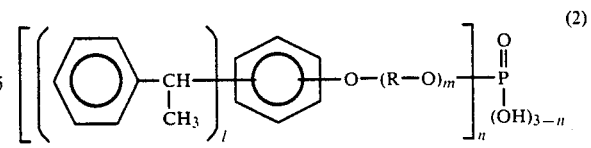

wherein R is a lower alkylene group, preferably ethylene or propylene group, l is an integer of 1 to 3, m is an integer of about 5 to 50 and n is an integer of 1 to 3, and an alkali metal salt thereof.

The alkali metal salt is formed at the OH groups of the phosphoric acid portion and its preferred examples are the sodium or potassium salts. The OH groups may be partially substituted.

The organic solvents useful in the invention are those which can dissolve TCMTB and are compatible with water. Examples of useful organic solvents include acetone, cyclohexanone, ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, tetrahydrofuran and dimethylformamide, among which diethylene glycol monomethyl ether, diethylene glycol monoethyl ether and dimethylformamide are preferred.

The above mentioned organic solvents possess sufficient solubility for TCMTB containing 20% or so of impure substances such as its dimer.

The amount of TCMTB in the composition of the invention is about 1 to 40% by weight, preferably 5 to 30% by weight. It is preferred that the ratio of TCMTB to STP is from about 1:0.5 to 1:6 by weight. The amount of STP is from about 5 to 40% by weight, preferably 6 to 30% by weight. The remainder is the organic solvent. The use of 40 or more % by weight of STP can well be an effective composition but is not recommended from an economical viewpoint.

The composition of the invention may be conveniently prepared by dissolving either TCMTB or STP in the organic solvent and then dissolving the other one, or, alternatively by dissolving a mixture of TCMTB and STP in the organic solvent.

The resulting composition can be stored and marketed as is. In addition, the composition may be diluted with water or a water-soluble organic solvent such as methanol, ethanol, ethylene glycol, propylene glycol, diethylene glycol or dipropylene glycol, to make a commercial product. When diluted with water, it is preferred to add an amount of 30 parts by weight or less to 100 parts by weight of the composition. Also, the water-soluble organic solvent is preferably added in an amount of 50 parts by weight to 100 parts by weight or less of the composition.

The composition of the invention is usually used by diluting with water to make about a 0.03 to 1% concentration of TCMTB. Such water-diluted solutions, when observed macroscopically, are a little white for a very few cases, but are clear solutions for almost all cases. The concentration of TCMTB as mentioned above is dependent upon the end use application. The water-diluted solution is typically used to treat natural materials such as wood, natural leathers, wet pulps and plant seeds.

On the other hand, the composition of the invention can be used directly, without dilution with water, for adhesives for wallpaper, starch containing preparations, sealants for caulking, metal-processing oils or the like.

The application of the subject compositions for the above mentioned materials can be carried out in accordance with conventional methods such as dipping, coating or pressure-injection.

Further, the compositions of the invention may contain an agent able to enhance antiseptic or antifungal effect or exert a synergistic effect thereof, e.g., 3-iodo-2-propargylbutylcarbamate or methylene bisthiocyanate. Other antiseptic or antifungal agents may be added to the subject compositions in an amount of 20% or less by weight of the composition provided that the total amount of TCMTB and the other antifungal agent is 1–40% by weight of the composition. Further, it is preferred that the ratio of TCMTB to the antifungal agent be from about 1:5 to 5:1 by weight.

When the composition is stored in an iron tank or used to dry wood or other natural materials, it is preferred to add another nonionic surfactant, such as a polyoxyethylene or polyoxypropylene block copolymer, to prevent or reduce turbidity in the composition. Suitable polymeric surfactants have a molecular weight of the polyoxypropylene group of about 3000 to 4000, and the ratio by weight of the polyoxypropylene group to the total weight of the block copolymer is about 10–30%. Preferably the ratio of the polyoxyethylene-polyoxypropylene block copolymer to STP is from about 5:1 to 1:5. The nonionic type surfactant may be used in an amount equal to or less than the amount of STP, provided that the total amount of STP and the nonionic type surfactant is 5–40% by weight of the composition.

The invention will be illustrated by the following examples. In the examples, "parts" mean "parts by weight".

EXAMPLE 1

| | | |
|---|---|---|
| (1) | Busan 80 (available from Buckman Labo. USA and containing 80% of TCMTB) | 25 parts |
| (2) | STP which has the formula | 25 parts |

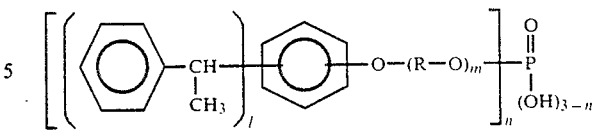

in which R is ethylene, l is 2 or 3, m is about 20 and n is about 1.

| | | |
|---|---|---|
| (3) | diethylene glycol monomethyl ether | 50 parts |

(1) was dissolved in (3), to which (2) was dissolved to make a solution, while stirring.

| | |
|---|---|
| (1) Busan 80 | 20 parts |
| (2) STP | 10 parts |
| (3) diethylene glycol monomethyl ether | 70 parts |

The above components were formulated in the same way as in Example 1.

EXAMPLE 3

| | |
|---|---|
| (1) Busan 80 | 40 parts |
| (2) STP | 20 parts |
| (3) diethylene glycol monomethyl ether | 40 parts |

The above components were formulated in the same way as in Example 1.

EXAMPLE 4

| | |
|---|---|
| (1) Busan 80 | 1.3 parts |
| (2) STP | 5 parts |
| (3) diethylene glycol monomethyl ether | 93.7 parts |

The above components were formulated in the same way as in Example 1.

EXAMPLES 5 AND 6

30 parts of diethylene glycol or water respectively were added to 100 parts of the solution of Example 1 to obtain a preparation of Example 5 or 6, respectively.

EXAMPLE 7

| | |
|---|---|
| (1) Busan 80 | 25 parts |
| (2) STP | 23 parts |
| (3) polyoxyethylene-polyoxypropylene block copolymer (MW of polyoxypropylene group is about 3000 to 4000 and the ratio of ethylene oxide to the total weight of the block copolymer is about 30%) | 10 parts |
| (4) diethylene glycol monomethyl ether | 42 parts |

(1) was dissolved in (4), to which (2) and (3) were dissolved, while stirring.

EXAMPLE 8

| | |
|---|---|
| (1) Busan 80 | 40 parts |
| (2) STP | 20 parts |
| (3) polyoxyethylene-polyoxypropylene block copolymer (as in Example 7) | 10 parts |
| (4) diethylene glycol monomethyl ether | 30 parts |

The above components were formulated in the same way as in Example 7.

EXAMPLE 9

80 parts of diethylene glycol and 20 parts of water were added to 100 parts of the preparation of Example 7.

EXAMPLE 10

| | |
|---|---|
| (1) Busan 80 | 12.5 parts |
| (2) 3-iodo-2-propargylbutyl carbamate (fungicide) | 10 parts |
| (3) STP | 15 parts |
| (4) diethylene glycol monomethyl ether | 62.5 parts |

After dissolving (2) in (4), (1) was added and lastly (3) was added to make a solution.

EXAMPLE 11

| | |
|---|---|
| (1) Busan 80 | 12.5 parts |
| (2) 3-iodo-2-propargylbutyl carbamate (fungicide) | 10 parts |
| (3) STP | 10 parts |
| (4) polyoxyethylene-polyoxypropylene block copolymer (as in Example 7) | 5 parts |
| (5) diethylene glycol monomethyl ether | 62.5 parts |

The above components were formulated in the same way as in Example 10.

EXAMPLE 12

| | |
|---|---|
| (1) Busan 80 | 12.5 parts |
| (2) methylene bisthiocyanate (fungicide) | 10 parts |
| (3) STP | 25 parts |
| (4) polyoxyethylene-polyoxypropylene block copolymer (as in Example 7) | 10 parts |
| (5) diethylene glycol monomethyl ether | 42.5 parts |

The above components were formulated in the same way as in Example 10.

EXAMPLE 13

| | |
|---|---|
| (1) Busan 80 | 25 parts |
| (2) sodium salt of STP | 25 parts |
| (3) diethylene glycol monomethyl ether | 50 parts |

The components were formulated in the same way as in Example 1.

COMPARATIVE EXAMPLE 1

| | |
|---|---|
| (1) Busan 80 | 25 parts |
| (2) polyoxyethylene nonylphenyl ether (10 mol addition of ethylene oxide) | 10 parts |
| (3) polyoxyethylene alkyl ether (50 mol addition of ethylene oxide and the alkyl is mixed alkyls having 16-18 carbon atoms | 15 parts |
| (4) diethylene glycol monomethyl ether | 50 parts |

(1) was dissolved in (4), to which (2) and (3) were added.

COMPARATIVE EXAMPLES 2-13

Instead of STP of Example 1, the following surfactants were used to prepare preparations analogous to that of Example 1.

2. polyoxyethylene nonylphenyl ether phosphoric acid ester (EO addition moles are 10)
3. polyoxyethylene lauryl ether phosphoric acid ester (EO addition moles are 10)
4. sodium alkyl diphenyl ether disulfonate (the alkyl contains 14-18 carbon atoms)
5. ammonium polyoxyethylene alkylphenyl ether sulfate (the alkyl contains 14-18 carbon atoms, EO addition moles are 10)
6. sodium alkylphenyl ether sulfate (the alkyl contains 14-18 atoms)
7. sodium lauryl sulfate
8. sodium dioctylsulfosuccinate
9. polyoxyethylene nonylphenyl ether (EO addition moles are 13)
10. polyoxyethylene alkyl ether (the alkyl contains 16-18 carbon atoms, and EO addition moles are 14)
11. polyoxyethylene-polyoxypropylene block copolymer (MW of polyoxypropylene group is about 3,000, and the ratio of EO to the total weight is 30%)
12. polyoxyethylene fatty acid ester (EO addition moles are 15)
13. polyoxyethylene sorbitan fatty acid ester (Ionet T-80C from Sanyo Chem., Ind., Ltd., of Japan)

TEST 1

Solubility

Each preparation of Examples 1-13 and Comparative Examples 1-13 were diluted with water to make 0.1% solution of TCMTB and its appearance observed.

The results are as follows.

(1) The preparations of Examples 2 and 3 were clearly solubilized; a little white color was macroscopically observed.

(2) The Preparations of Examples 1, 4-6 and 7-12 were completely clearly solubilized.

(3) The preparations of Examples 1-13 after the dilution were not changed on appearance after one month's storage.

(4) The preparations of Comparative Examples 1-13 became homogeneous emulsions immediately after the dilution, but formed a precipitate after a few days to one week.

TEST 2

Permeability

Each preparation of Example 1 and Comparative Example 1 was diluted with industrial water 100 times (TCMTB concentration: 0.2%) and injected under pressure into American hemlock (square timber of 100×100×600 mm). The square timber after injection was cut off at the positions of 100, 200 and 300 mm from a cross-section of wood where the active ingredient (Kg/m$^3$) was determined by a chemical analysis.

The results are as follows.

| | Injection Kg/m$^3$ | TCMTB Kg/m$^3$ | | |
|---|---|---|---|---|
| | | 100 mm | 200 mm | 300 mm |
| Example 1 | 354 | 2.4 | 2.2 | 1.6 |
| Comparative Example 1 | 271 | 2.3 | 1.6 | 1.1 |

As is clear from the Table, a water-diluted clear solution of Example 1 is much more deeply penetrated from the surface of the wood than a water-diluted emulsion of Comparative Example 1.

The water-soluble composition of TCMTB in accordance with this invention can be stored in its clear solution form for a long period, without or with dilution with water or organic solvents and hence is superior to the conventional emulsion of TCMTB which is unstable during a long period of storage.

We claim:

1. A water-soluble antiseptic or antifungal composition which comprises 2-(thiocyanomethylthio) benzothiazole in an amount of 1-40% by weight of the composition, a polyoxyalkylene styrylphenyl ether phosphoric acid ester or alkali metal salt thereof in an amount of 5-40% by weight of the composition, and an organic solvent which can dissolve the above benzothiazole compound and is compatible with water, said phosphoric acid ester having the formula

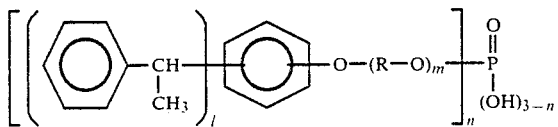

in which R is a lower alkylene group, $l$ is an integer of 1-3, m is an integer of about 5-50 and n is an integer of 1-3.

2. The composition of claim 1 wherein the benzothiazole compound is present in an amount of 5-30% by weight.

3. The composition of claim 1 wheein the benzothiazole compound is about 80% pure.

4. The composition of claim 1 wherein the polyoxyalkylene styrylphenyl ether phosphoric acid ester or alkali metal salt is present in an amount of 6-30% by weight.

5. The composition of claim 1 wherein the polyoxyalkylene group is polyoxyethylene or polyoxypropylene.

6. The composition of claim 1 wherein the organic solvent is diethylene glycol monomethylether, diethylene glycol monoethylether or dimethylformamide.

7. The composition of claim 1 which further contains a surfactant of a polyoxyethylene-polyoxypropylene block copolymer wherein the molecular weight of the polyoxypropylene group is about 3000 to 4000 and the ratio of the polyoxypropylene group to the total weight of the block copolymer is about 0-30% by weight.

8. The composition of claim 7, wherein the ratio of said block copolymer to said phosphoric acid ester is from about 5:1 to 1:5 by weight.

9. The composition of claim 1 further containing an additional antifungal or antiseptic agent in an amount up to 20% by weight of the composition with the proviso that the antifungal or antiseptic agent and the 2-(thiocyanomethylthio) benzothiazole together do not exceed 40% by weight of the composition.

10. The composition of claim 9 wherein said antifungal agent is 3-iodo-2-propargylbutylcarbamate.

11. The composition of claim 9 wherein said antifungal agent is methylene bisthiocyanate.

12. The composition of claim 1 further containing up to 30 parts by weight of water per 100 parts by weight of said composition.

13. The composition of claim 1 further containing up to 50 parts by weight of a water soluble alcohol per 100 parts by weight of said composition.

14. A method of treating wood leather, wet pulp and plant seeds to preserve them which comprises applying an aqueous solution comprising 2-(thiocyanomethylthio)benzothiazole in a concentration of from about 0.03 to about 1% by weight, said aqueous solution further containing polyoxyalkylene styrylphenyl ether phosphoric acid ester of the formula

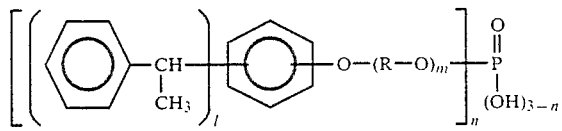

in which R is a lower alkylene group, $l$ is an integer of 1-3, m is an integer of about 5-50 and n is an integer of 1-3.

* * * * *